United States Patent [19]
Kondoh et al.

[11] Patent Number: 5,436,362
[45] Date of Patent: Jul. 25, 1995

[54] METHOD OF PRODUCING DIALKYLCARBONATE

[75] Inventors: Tadami Kondoh; Yoshimi Okada; Fumiaki Tanaka; Sachio Asaoka, all of Kanagawa; Susumu Yamamoto, Yokohama, all of Japan

[73] Assignee: Chiyoda Corporation, Japan

[21] Appl. No.: 152,691

[22] Filed: Dec. 16, 1993

[30] Foreign Application Priority Data

Nov. 20, 1992 [JP] Japan ................................ 4-333858
Jun. 4, 1993 [JP] Japan ................................ 5-160434

[51] Int. Cl.$^6$ .............................................. C07C 69/96
[52] U.S. Cl. ................................................ 558/277
[58] Field of Search ........................................ 558/277

[56] References Cited

U.S. PATENT DOCUMENTS

| | | |
|---|---|---|
| 3,642,858 | 2/1972 | Frevel et al. .......................... 558/277 |
| 3,803,201 | 4/1974 | Gilpin et al. .......................... 558/277 |
| 4,062,884 | 12/1977 | Romano et al. ....................... 558/277 |
| 4,181,676 | 1/1980 | Buysch et al. ..................... 558/277 X |
| 4,307,032 | 12/1981 | Krimm et al. ........................ 558/277 |
| 4,434,105 | 2/1984 | Buysch et al. ..................... 558/277 X |
| 4,734,518 | 3/1988 | Knifton ................................. 558/277 |
| 5,214,182 | 5/1993 | Knifton ................................. 558/277 |
| 5,218,135 | 6/1993 | Buysch et al. ........................ 558/277 |
| 5,231,212 | 7/1993 | Buysch et al. ........................ 558/277 |

Primary Examiner—Mary C. Lee
Assistant Examiner—Michael G. Ambrose
Attorney, Agent, or Firm—Lorusso & Loud

[57] ABSTRACT

In a method of producing dialkylcarbonate, alcoholic compound and cyclo-carbonate are subjected to a catalytic reaction each other at a reaction temperature of 20° to 200° C. and under a pressure of 0 to 40 kg/cm$^2$G, which keeps the reaction system liquid, in the presence of ion exchanged zeolite which is ion-exchanged with alkali metal ion and/or alkaline earth metal ion.

11 Claims, No Drawings

METHOD OF PRODUCING DIALKYLCARBONATE

BACKGROUND OF THE INVENTION

1. Field of the Invention

This invention relates to a method of producing dialkylcarbonate using both an alcoholic compound and a cyclocarbonate as raw material in the presence of an ion-exchanged zeolite which is ion-exchanged with an alkali metal ion and/or alkaline earth metal ion.

2. Description of the Related Art

As a method of producing dialkylcarbonate through reaction of alcohol and cyclocarbonate, there has been conventionally known a method of reacting methanol with ethylene carbonate in the presence of a homogeneous or heterogeneous catalyst to produce dimethylcarbonate and ethylene glycol.

In the method utilizing the homogeneous catalyst, an amine such as triethylamine, an alkali metal such as sodium, an alkali metal compound such as sodium chloroacetate or sodium methylate, or a thallium compound has been used as the catalyst for the reaction.

In the method utilizing the heterogeneous catalyst, ion exchange resins have been conventionally proposed as catalysts. For example, Japanese Laid-open Patent Application No. 64-31737 proposes the heterogeneous catalysis using, as a catalyst, ion exchange resins having various kinds of functional groups, amorphous silica into which alkali and alkaline earth metal silicate are impregnated, or ammonium-ion-exchanged zeolite having a Y-structure (hereinafter referred to as Y-zeolite).

In the conventional reaction methods using the catalysts as described above, the reaction method using the heterogeneous catalysis is more preferably used for industrial application than the reaction method using the homogeneous catalysis because the reaction product mixture and catalyst can be more easily separated from each other in the former than in the latter.

However, when the ion exchange resins or the silica impregnated with alkali and alkaline earth metal silicate as described above are used as the catalyst, catalytic active sites irregularly exist, and thus they are inhomogeneously distributed. Therefore, it is considered that catalytic activity cannot be improved using these catalysts.

On the other hand, in using a zeolite catalyst it is expected that homogeneous catalytic active sites can be formed because cations can be contained in polyanionic framework cavities of the three-dimensional framework structure of aluminosilicic acid constituting crystalline aluminosilicate. Generally, positive ions exist to balance the electrostatic charge in the polyanionic framework structure of the zeolite. Further, the zeolite catalyst has excellent heat-resistance and thus it is usable for a reaction at a high temperature if occasion demands, so that it is considered to be favorable as a catalyst.

However, the catalytic activity of the above-described ammonium-ion exchanged Y-zeolite catalyst is considered to be low because the component is volatile and thus the active sites are unstable. Actually, in a comparison example as described later, the appearance of catalytic activity of the zeolite catalyst for a conversion reaction was not observed at a reaction temperature of 50° C.

An ion exchange resin catalyst has inferior organic solvent resistance, especially upon heating. The ion exchange resin catalyst gradually deteriorates, and finally loses catalytic activity due to elution of the functional groups and loss of catalytically active sites over a long period of service.

When the catalytic activity is low, the reaction temperature must be increased in order to raise the reaction rate and improve conversion efficiency to make up for lack of catalytic activity. However, the ion exchange resin has low heat-stability as above described, and thus the reaction temperature is limited to about 100° C. at maximum. Particularly for the ammonium-ion exchanged zeolite catalyst, the reaction temperature cannot be increased while stably keeping the catalytic activity thereof because the ammonium component is volatile. Therefore, process control and operation are complicated for an industrial use of the ion exchange resins and the ammonium-ion exchanged zeolite.

SUMMARY OF THE INVENTION

An object of this invention is to provide a heterogeneous catalyst which can be suitably used for a method of producing a dialkylcarbonate through the reaction of an alcoholic compound and to cyclo-carbonate, to maintain high catalytic activity through the whole reaction process, to improve the reaction rate by adopting a high reaction temperature above 100° C. in accordance with conditions, and to provide for easy separation of the catalyst from the reaction product mixture.

Another object of this invention is to provide a method of producing a dialkylcarbonate from an alcohol and a cyclocarbonate with high conversion efficiency using the catalyst as described above.

In order to attain the above objects, the inventors have made an intensive study of zeolite catalysts having more homogeneously distributed, catalytically active sites and better heat resistance and organic solvent-resistance than ion exchange resins and the ammonium-ion exchanged zeolite. Through this study, they have made this invention.

According to this invention, a method of producing dialkylcarbonate is characterized in that alcoholic and cyclocarbonate compounds are subjected to a catalytic reaction at a reaction temperature of 20° to 200° C., preferably 50° to 180° C. and under a pressure of 0 to 40 kg/cm$^2$G, preferably 0 to 26 kg/cm$^2$G, which keep the reactant in liquid state, in the presence of an ion exchanged zeolite, which is ion-exchanged with alkali metal ion and/or alkaline earth metal ion.

In this invention, "zeolite which is ion-exchanged (ion-exchanged zeolite)" means a zeolite whose ion-exchange sites are exchanged with alkali metal cations and/or alkaline earth metal cations. That is, it is defined as a zeolite whose ion exchange sites are occupied by one or more kinds of alkali or alkaline earth metal cations.

Particularly, the zeolite catalyst is most preferably a zeolite having an A-structure (hereinafter referred to as A-zeolite) or X-structure (hereinafter referred to as X-zeolite) in which 50% or more of ion exchange sites are ion-exchanged (occupied) with potassium ion (K+). In this case, if the ion exchange efficiency of potassium ion (K+) in the above zeolite is less than 100%, the residual ion-exchange sites are preferably ion-exchanged (occupied) with other alkali metal ions and/or alkaline earth metal ions.

According to this invention, the zeolite which is used for the catalytic reaction has homogeneous catalytically active sites, so that a dialkylcarbonate can be produced with high conversion efficiency from an alcohol and a cyclocarbonate.

In the zeolite used in this invention, the ion-exchange sites thereof are exchanged with alkali metal or alkaline earth metal ions, so that the zeolite keeps its stable catalytic activity under the conditions of temperature and pressure at which alcohol such as methanol and cyclocarbonate such as ethylene carbonate can be reacted.

Further, according to this invention, the cyclocarbonate conversion efficiency can be further improved by using an A-zeolite having the mole ratio of $SiO_2/Al_2O$ of 2 or X-zeolite having the mole ratio of $SiO_2/Al_2O_3$ of 2.4 to 2.5. Both A-zeolite and X-zeolite are suitable catalysts because they have a larger ion exchange capacity than normal ion exchange resins.

According to this invention, in the method of conducting the catalytic reaction of an alcohol and a cyclocarbonate to form dialkylcarbonate and alkylene glycol, zeolite, which has excellent heat-resistance and excellent resistance to organic-solvent and is low in cost, is subjected to the ion exchange treatment, so that the catalytically active sites can be more homogeneously distributed on the zeolite than on the ion exchange resin catalyst which has been conventionally mainly used. In addition, the exchange ion is alkali metal and/or alkaline earth metal, so that stable catalytic activity can be obtained under a temperature above 100° C.

As described above, according to this invention, the stable and homogeneous catalytic activity can be maintained throughout the whole reaction process, and dialkylcarbonate of high concentration can be obtained with high conversion efficiency.

DETAILED DESCRIPTION OF THE PREFERRED EMBODIMENTS

The reaction of an alcohol and a cyclocarbonate according to this invention has been well known as noted above, and commercial products generally available in the market can be used as the cyclocarbonate and alcohol raw materials for the reaction. Ordinarily, the commercial products can be used directly or after being subjected to a dehydration treatment.

No limitation is imposed on the raw cyclocarbonate which is used in this invention. However, lower alkylene cyclocarbonate such as ethylene carbonate, propylene carbonate, butylene carbonate or the like is preferably used as the raw cyclocarbonate, and ethylene carbonate or propylene carbonate is most preferably used.

No limitation is imposed on the alcohol reactant, provided the alcohol reacts with cyclocarbonate to produce the carbonate product. However, an aliphatic or aromatic alcohol having 1 to 10 carbon atoms is preferably used. For example, methanol, ethanol, n-propanol, iso-propanol, n-butanol, iso-butanol, secondary butanol, tertiary butanol, allyl alcohol, pentanol, cyclo-hexanol, benzyl alcohol, 2-phenyl ethyl alcohol, 3-phenyl propyl alcohol, 2-methoxy ethanol or the like can be used as the aliphatic or aromatic alcohol. Particularly, a lower aliphatic alcohol is most preferably used.

Further, a phenolic compound can be used in place of the alcoholic compound as the compound which has a hydroxyl (OH) group and reacts with cyclocarbonate to produce the carbonate.

Natural or synthetic zeolite can be used as the zeolite which is used as a catalyst in this invention, and synthetic zeolite is generally preferably used because it is more homogeneous and thus the desired quality can be kept. The mole ratio of $SiO_2/Al_2O_3$ in the usually-used zeolite is 2 to 100. Preferably, the mole ratio is 2 to 6, and most preferably it is 2 to 3.

Specifically, in this invention the favored zeolite is of the LTA type (containing A-zeolite), FAU type (containing X-zeolite and Y-zeolite), LTL type (containing L-zeolite having L-structure), MOR type, MAZ type (containing Ω-zeolite having Ω-structure), FER type and/or MFI type (containing ZSM-5). Most preferably, the zeolite is of the LTA type or FAU type (especially X-zeolite). These zeolites have the structures of the known zeolites published in "The Structure Commission of the International Zeolite Association" (Atlas of Zeolite Structure Type, W. M. Meier and D. H. Olson (1987)).

In this invention it is preferred that 50 weight % or more of the zeolite have an average crystal diameter of about 30 $\mu$m or smaller, most preferably about 10 $\mu$m or smaller.

The catalytic reaction producing dialkylcarbonate in this invention is carried out in the presence of the alkali metal and/or alkaline earth metal exchanged zeolite which is obtained by exchanging the ion exchange sites of the above zeolite for ions of alkali metal (Li, Na, K, Rb, Cs) and/or alkaline earth metal (Be, Mg, Ca, Sr, Ba) belonging to Ia group and/or IIa group in the periodic table of elements.

The ion-exchanged zeolite catalyst as described above can be a zeolite which is produced in such a manner that desired alkali metal and/or alkali earth metal cations (hereinafter referred to as "alkali, etc. metal cations") occupy the ion-exchange sites. For example, Na form A-zeolite, Na form X-zeolite or the like in which the ion-exchange sites are occupied by sodium ions can be used as the ion-exchanged zeolite catalyst. Further, all or a part of the sodium ions occupying the ion-exchange sites of these Na form zeolites can be exchanged with other alkali metal and/or alkaline earth metal ions, for example, potassium ion. Still further, a zeolite, which is obtained by ion-exchange treatment of the above-mentioned zeolites to introduce the desired alkali, etc. metal cations into the ion-exchange sites, can be used. An inorganic salt such as nitrate or chloride, or salt of organic acid such as acetate can be used as an alkali metal cation source for the ion exchange treatment.

Further, a zeolite which includes a proper amount of desired alkali, etc. metal cations, at locations other than the ion-exchange sites, in addition to the alkali, etc. metal cations at the ion-exchange sites, can be used. These zeolite catalysts can be prepared by treating the alkali, etc. metal cation-exchanged zeolite as described above with a solution containing alkali, etc. metal cations, using an impregnation method or a spray method.

The form of the above zeolite catalyst is not particularly limited, and it can ordinarily be used in various forms such as powder, particles, spheres, pellets, beads or the like. These various forms can be obtained by adding a binder such as clay mineral, alumina, silica or the like to the zeolite. A mixture of the zeolite and the binder is formed as a cylindrical shape, a granule, a sphere, a pellet or the like shape by means of extrusion molding, spray drying, tableting press, tumbling or an oil drop method.

Further, a metal component such as tin, lead, zinc, titanium or the like can be loaded on the above zeolite by ion exchange or impregnation as an auxiliary catalytic component.

In this invention, as the carbon number of the alcohol reactant increases, the reactivity is lowered. Therefore, in order to heighten the reactivity, the reaction must be carried out at a higher temperature within a temperature range as described later. In this case, the conventional ion-exchange resin catalyst has low heat-stability, and it is unsuitable for an industrial application. On the other hand, as described above, the zeolite catalyst of this invention has higher heat-stability, and a stable catalytic reaction can be carried out irrespective of the carbon number of the alcohol reactant, so that it can be suitably used for industrial applications.

The catalyst in this invention is subjected to drying under heated nitrogen or air before being used. The range of the drying temperature is selected so that the crystal structure of the zeolite is not damaged, suitably 200° to 600° C. in general. Degraded, used catalyst also can be reactivated by the same kind of heat treatment.

The reactor type in this invention is not specifically limited but can be any generally known one such as a continuous fluid bed, fixed bed or stirred tank, etc. Using any of these reactors, alcohol and cyclocarbonate, as the raw materials, can be converted to dialkylcarbonate using the zeolite catalyst cation-exchanged with alkali, etc. metal cations.

The reaction system of this invention is not specifically limited, and generally well-known reaction systems such as a flow system using a fluid bed or a fixed bed, a stirring system or the like can be used. Using these reaction systems, raw materials of alcohol and cyclocarbonate are subjected to the conversion reaction in the presence of the alkali, etc. metal cation-exchanged zeolite catalyst to obtain dialkylcarbonate.

The method of this invention can be carried out in a continuous reaction or a batch reaction, and one of these can be suitably selected and used in combination with a reaction system in accordance with its purpose.

The reaction conditions of this invention are as follows: the reaction temperature, 20° to 200° C., preferably 50° to 180° C.; the reaction pressure, 0 to 40 kg/cm$^2$G, preferably 0 to 26 kg/cm$^2$G which keeps the reactant in liquid state; and liquid space velocity (LHSV) in the fluid reaction system, 0.2 to 10 hr$^{-1}$.

If the reaction temperature is lower than 20° C., the reaction rate would be lowered, and thus become impractical. Further, if the temperature is higher than 200° C., an unfavorable side reaction such as thermal decomposition of the cyclocarbonate would occur. If the reaction pressure is a vacuum, the reaction does not proceed. In this invention the reaction is usually carried out under the autogenous pressure which keeps the system liquid at the reaction temperature. Further, if the pressure is increased over 40kg/cm$^2$G, the reaction is not promoted.

If the LHSV in the fluid reaction system is lower than 0.1 hr$^{-1}$, the capacity to be treated is insufficient, and becomes impractical. On the other hand, if the LHSV exceeds 1 Ohr$^{-1}$, the conversion of the reaction is extremely low, and this is unfavorable.

The temperature and the pressure as described above are selected to keep the reaction system, including the reaction raw materials and the reaction products, in a liquid state. The method of this invention can be carried out in the presence of an inert solvent such as benzene, toluene or the like.

According to this invention, the raw materials of alcohol and cyclocarbonate are preferably supplied to a reaction area under the reaction conditions as described above and in a mole ratio of alcohol/cyclocarbonate which is about 2 to 20. If the mole ratio is lower than about 2, the conversion efficiency is lowered. On the other hand, if the mole ratio is higher than 20, this would increase the recovery rate of the raw alcohol and lower the process efficiency, and thus become impractical.

In this invention, an alcohol and a cyclocarbonate react as described above to thereby produce the desired dialkylcarbonate together with alkylene glycol. The reaction product mixture thus obtained is subsequently subjected to a prescribed purification treatment such as distillation to separate the starting materials from the reaction products, and thereafter the dialkylcarbonate and alkylene glycol are separated from each other. Further, the non-reacted raw materials can be recovered and recycled. In the continuous fluid system, the recovered raw materials are recycled to the raw material supply point and re-used.

EXAMPLES

This invention will be hereunder described in more detail on the basis of the following embodiments, however, this invention is not limited to the following embodiments.

In the following embodiments, the conversion efficiency is calculated in accordance with the following equation:

Conversion efficiency
(%)=dialkylcarbonate(mole)/raw
cyclo-carbon(mole)×100

In this case, hydroxyalkylene-alkylcarbonate is produced as an intermediate product, and it further reacts with the alcohol to produce dialkylcarbonate. Therefore, the calculation of the conversion efficiency is carried out on the assumption that the amount of the above hydroxyalkylene-alkylcarbonate does not contribute to the amount of the dialkycarbonate product.

Embodiments 1 to 3

Three commercial types of powdery, alkali-ion exchanged Azeolite having a SiO$_2$/Al$_2$O$_3$ mole ratio of 2 (produced by Union Carbide Co., Ltd.) were used as the zeolite catalyst after drying. Specifically, they were potassium-ion exchanged A-zeolite (K form A-zeolite; brand name: 3A powder), sodium-ion exchanged zeolite (Na form A-zeolite; brand name: 4A powder) and calcium-ion exchanged zeolite (Ca form A-zeolite; brand name: 5A powder) as shown in the following TABLE 1.

10 g powder of each alkali-ion exchanged zeolite as shown in TABLE 1 and 235 g of a mixture of methanol and ethylene carbonate (mole ratio of methanol/ethylene carbonate=4) were supplied to a 300 ml-volume flask equipped with a cooler and a stirrer, and the mixture was stirred while kept at 50° C.

The reaction products were analyzed using gas chromatography. The analysis of the reaction products by gas Chromatography after five hours in the reaction process are shown in the following TABLE 1.

TABLE 1

| EMBODIMENT | CATALYST | *1 | *2 | *3 |
| --- | --- | --- | --- | --- |
| 1 | 3A powder (K form A-zeolite) | 54.9 | 22.7 | 15.5 |
| 2 | 4A powder (Na form A-zeolite) | 22.5 | 9.3 | 6.4 |

TABLE 1-continued

| EMBODIMENT | CATALYST | *1 | *2 | *3 |
|---|---|---|---|---|
| 3 | 5A powder (Ca form A-zeolite) | 1.6 | 0.6 | 0.4 |

*1: Conversion efficiency (%) of ethylene carbonate
*2: Concentration (weight %) of dimethylcarbonate
*3: Concentration (weight %) of ethylene glycol

Embodiment 4

Commercial pelletized potassium ion (K+) exchange A-zeolite (produced by Union Carbide Co., Ltd., brand name: 3A pellet) was pulverized and then sieved using a mesh of 16 to 24. The reaction was carried out using a continuous fixed-bed reactor charged with the sieved zeolite as the catalyst.

The reaction conditions were as follows: temperature, 90° C.; pressure 7 kg/cm$^2$; liquid space velocity(LHSV), 1 hr$^{-1}$; amount of catalyst, 10 ml; and raw materials, methanol/ethylene carbonate mole ratio=4.

The reaction products were analyzed using gas chromatography as in embodiment 1. The results were as follows: after 42 hours from the start of the supply of the raw material liquid, the conversion efficiency of ethylene carbonate, 6.6%; concentration of dimethylcarbonate, 2.8 wt.%; and concentration of ethylene glycol, 1.9 wt %.

Embodiment 5

The reaction was carried out in the same manner as the embodiment 4, except for the reaction temperature of 120° C. and the pressure of 10 kg/cm$^2$, LHSV of 0.3 hr$^{-1}$, and the reaction products were analyzed by gas chromatography after 50 hours had elapsed from the start of the supply of the raw material liquid. The results were as follows: conversion efficiency of ethylene carbonate, 42.5%; concentration of dimethylcarbonate, 18.0 wt. %; and concentration of ethylene glycol, 13.0 wt. %.

Comparative Example

The reaction was carried out in the same manner as the embodiment 1, except for use of a catalyst of commercial ammonium ion exchanged Y-zeolite having a SiO$_2$/Al$_2$O$_3$ mole ratio of 4.8 (NH$_4$ form Y-zeolite, brand name: SK41, produced by Union Carbide Co., Ltd.).

The results were as follows: conversion efficiency of ethylene carbonate after five hours had elapsed in the reaction process was 0%, and no production of dimethylcarbonate was observed.

Embodiments 6 to 10

The reaction was carried out in the same manner as the embodiment 1, except for use of the following catalysts:

sodium ion exchanged Y-zeolite having a SiO$_2$/Al$_2$O$_3$ mole ratio of 4.6 (Na form Y-zeolite, brand name: SK-40, produced by Union Carbide Co., Ltd.) (Embodiment 6);

lithium-ion exchanged Y-zeolite (Li form Y-zeolite) obtained by ion-exchanging Y-zeolite having a SiO$_2$/Al$_2$O$_3$ mole ratio of 5.5 (produced by Toso Co., Ltd.) with lithium ion (Embodiment 7);

potassim-ion exchanged X-zeolite (K form X-zeolite) obtained by ion-exchanging X-zeolite having a SiO$_2$/Al$_2$O$_3$ mole ratio of 2.4 (produced by Union Showa Co., Ltd.) with potassium ion ( Embodiment 8);

potassium-ion exchanged L-zeolite having a SiO$_2$/Al$_2$O$_3$ mole ratio of 5.4 (K form L-zeolite, brand name: SK-45, produced by Union Carbide) (Embodiment 9); and sodium ion exchanged X-zeolite having a SiO$_2$/Al$_2$O$_3$ mole ratio of 2.4 (Na form X-zeolite, brand name: 13X, produced by Union Showa Co., Ltd. ) (Embodiment 10).

The reaction products after five hours had elapsed were analyzed by gas chromatography as in embodiment 1, and the results are shown in the following TABLE 2.

TABLE 2

| EMBODIMENT | CATALYST | *1 | *2 | *3 |
|---|---|---|---|---|
| 6 | Na form Y-zeolite | 7.9 | 3.8 | 2.3 |
| 7 | Li form Y-zeolite | 1.9 | 0.8 | 0.6 |
| 8 | K form X-zeolite | 24.5 | 10.2 | 7.0 |
| 9 | K form L-zeolite | 10.1 | 4.2 | 2.9 |
| 10 | Na form X-zeolite | 19.9 | 8.3 | 5.7 |

*1: Conversion efficiency (%) of ethylene carbonate
*2: Concentration (weight %) of dimethylcarbonate
*3: Concentration (weight %) of ethylene glycol

Embodiment 11

The reaction was carried out in the same manner as in embodiment 1, except that ethanol was used as the alcohol reactant, 250 g of the ethanol and ethylene carbonate (mole ratio of ethanol/ethylene carbonate=4) were used, and the reaction temperature was 70° C. The reaction mixture after five hours had elapsed in the reaction process were analyzed by gas chromatography as in embodiment 1.

The results were as follows: Conversion efficiency of ethylene carbonate to diethylcarbonate, 6.4 %; concentration of diethylcarbonate, 2.8 wt %; and concentration of ethylene glycol, 1-5 wt %.

Embodiment 12

8 g of dried commercial potassium ion exchanged A-zeolite powder, having a SiO$_2$/Al$_2$O$_3$ mole ratio of 2 (produced by Union Showa Co., Ltd., brand name: zeolite 3A), and 200 g of a mixture of n-propanol and ethylene carbonate (mole ratio of n-propanol/ethylene carbonate=4) were supplied to a 300 ml-volume autoclave equipped with a stirrer, and the mixture was reacted under the following conditions: temperature: 100° C., pressure: 1.5 kg/cm$^2$G and rotation of the stirrer: 800 rpm. The reaction mixture, after four hours had elapsed in the reaction process, was analyzed using gas chromatography. The results were as follows: conversion efficiency of ethylene carbonate to dipropylcarbonate, 2.0%.

Embodiments 13 to 15

Na form A-zeolite having a SiO$_2$/Al$_2$O$_3$ mole ratio of 2 (produced by Union Showa Co., Ltd., brand name: zeolite 4A) was 50% or more ion-exchanged with potassium ions using potassium nitrate as shown in TABLE 3, and then dried to prepare a Na/K form A-zeolite in which 50% or more of the ion exchange sites were exchanged with potassium ions and the other ion exchange sites were exchanged with sodium ions.

The reaction was carried out in the same manner as embodiment 1, except that 10 g of powder of the above-obtained zeolite was used as a catalyst, and 250 g of raw material of methanol and ethylene carbonate (mole ratio of methanol/ethylene carbonate=4) were used.

The reaction mixture after five hours had elapsed in the reaction process was analyzed by gas chromatography. The results were as shown in TABLE 3.

TABLE 3

| EMBODIMENT | CATALYST $K^+$R.I. | *1 | *2 | *3 |
|---|---|---|---|---|
| 13 | 50% | 27.7 | 11.6 | 8.0 |
| 14 | 63% | 54.8 | 22.8 | 15.7 |
| 15 | 94% | 57.0 | 23.8 | 16.4 |

$K^+$R.I.: Sites ion-exchanged with potassium ion ($K^+$)
*1: Conversion efficiency (%) of ethylene carbonate
*2: Concentration (weight %) of dimethylcarbonate
*3: Concentration (weight %) of ethylene glycol Embodiment 16

The reaction was carried out in the same manner as embodiment 12, except that 250 g of a mixture of methanol and ethylene carbonate (mole ratio of methanol/ethylene carbonate=2) were used as raw material, 10 g of a K form A-zeolite which was obtained by further ion-exchanging the same zeolite (brand name: zeolite 3A, produced by Union Showa Co., Ltd.) as used in embodiment 12 with potassium ion was used as a catalyst, and the reaction temperature and pressure were 100° C. and 3.5 kg/cm², respectively.

The reaction mixture, after four hours had elapsed in the reaction process, was analyzed by gas chromatography. The results were as follows: conversion efficiency of ethylene carbonate, 35.7%; concentration of dimethylcarbonate, 21.1 wt %; and concentration of ethylene glycol, 13.8 wt %.

Embodiment 17

The reaction was carried out in the same manner as embodiment 16, except that 250 g of a mixture of methanol and ethylene carbonate (mole ratio of methanol/ethylene carbonate=8) were used as the raw material.

The reaction mixture after two hours had elapsed in the reaction process was analyzed by gas chromatography. The results were as follows: conversion efficiency of ethylene carbonate, 68.4%; concentration of dimethylcarbonate, 17.9 wt %; and concentration of ethylene glycol, 13.5 wt %.

Embodiment 18

The reaction was carried out in the same manner as embodiment 16, except that 250 g of a mixture of methanol and ethylene carbonate (mole ratio of methanol/ethylene carbonate=4) were used as the raw material and the reaction temperature and pressure were 160° C. and 13.5 kg/cm².

The reaction mixture after two hours had elapsed in the reaction process was analyzed by gas chromatography. The results were as follows: conversion efficiency of ethylene carbonate, 50.8%; concentration of dimethylcarbonate, 21.8 wt %; and concentration of ethylene glycol, 15.9 wt %.

Embodiment 19

The same zeolite (brand name: zeolite 4A, produced by Union Showa Co., Ltd. ) as used in embodiment 13 was ion-exchanged with rubidium acetate to prepare rubidium (Rb) ion-exchanged A-zeolite (Na/Rb form A-zeolite) and subjected to drying and firing at 450° C. in an air atmosphere.

The above obtained 10 g of Na/Rb form A-zeolite powder and 250 g of a mixture of methanol and ethylene carbonate (mole ratio of methanol/ethylene carbonate=4) were supplied to a 300 ml-volume autoclave equipped with a stirrer, and they reacted under the conditions: temperature at 100° C., pressure of 3.5 kg/cm²G and rotation of the stirrer at 800 rpm.

The reaction mixture after two hours had elapsed in the reaction process was analyzed using gas chromatography. The results were as follows: conversion efficiency of ethylene carbonate, 42.0%; concentration of dimethylcarbonate, 17.7 wt %; and concentration of ethylene glycol, 12.2 wt %.

Embodiment 20

The cesium(Cs) ion-exchanged A-zeolite (Na/Cs form A-zeolite) was prepared in the same manner as embodiment 19, except for ion-exchanging with cesium acetate.

The reaction was carried out in the same manner as embodiment 19, except that the obtained Na/Cs form A-zeolite was used as the catalyst.

The reaction mixture after two hours had elapsed in the reaction process was analyzed using gas chromatography. The results were as follows: conversion efficiency of ethylene carbonate, 37.7%; concentration of dimethylcarbonate, 15.7 wt %; and concentration of ethylene glycol, 10.8 wt %.

As is apparent from the embodiments and the comparative examples described above, the reaction did not proceed at a reaction temperature of 50° C. in the case where the ammonium-ion exchanged zeolite, which is conventional, was used for the reaction of methanol and ethylene carbonate, which is one kind of cyclocarbonate. On the other hand, in the case where the alkali metal and/or alkali earth metal ion exchanged zeolite of this invention was used, the reaction with the ethylene carbonate proceeded at the reaction temperature of 50° C., although the reaction rate was different in accordance with the carbon number of carbon atoms in the alcohol and its type. In addition, as the reaction temperature was increased, the conversion efficiency of ethylene carbonate was also increased.

Further, in the case where the alkali metal and/or alkali earth metal ion exchanged zeolite was used, it was found that the conversion efficiency of ethylene carbonate varied in accordance with the mole ratio of $SiO_2$/$Al_2O_3$ and the alkali metal or alkali earth metal ion-exchanged, and when A-zeolite was used after ion-exchange with potassium or sodium ions of alkali metal, the catalytic activity of the zeolite catalyst was improved.

What is claimed is:

1. A method of producing dialkylcarbonate, which comprises reacting an alcoholic compound with a cyclocarbonate at 20° to 200° C. in liquid phase and in the presence of a zeolite which is ion-exchanged with alkali metal ion and/or alkaline earth metal ion.

2. The method as claimed in claim 1, wherein said zeolite has a mole ratio of $SiO_2$/$Al_2O_3$ in the range of 2 to 3 and a structure which is A-type or X-type.

3. The method as claimed in claim 1, wherein the mole ratio of the alcoholic compound to the cyclo-carbonate is in the range of 2 to 20.

4. The method as claimed in claim 1, wherein the reaction temperature is above 100° C.

5. The method as claimed in claim 1, wherein the is ion-exchanged with potassium ion.

6. The method as claimed in claim 1, wherein the zeolite is ion-exchanged with rubidium ion.

7. The method as claimed in claim 1, wherein the zeolite is ion-exchanged with cesium ion.

8. The method as claimed in claim 1, wherein 50% or more of ion exchange sites of the zeolite are occupied by potassium ion, and the other ion exchange sites are occupied by other alkali metal ions and/or alkaline earth metal ions.

9. The method as claimed in claim 1, wherein the alcoholic compound is methanol, and the cyclocarbonate is ethylene carbonate.

10. The method as claimed in claim 1, wherein the alcoholic compound is ethanol, and the cyclocarbonate is ethylene carbonate.

11. The method as claimed in claim 1, wherein the alcoholic compound is propanol, and the cyclocarbonate is ethylene carbonate.

* * * * *

UNITED STATES PATENT AND TRADEMARK OFFICE
CERTIFICATE OF CORRECTION

PATENT NO. : 5,436,362

DATED : July 25, 1995

INVENTOR(S) : KONDOH et al

It is certified that error appears in the above-indentified patent and that said Letters Patent is hereby corrected as shown below:

On the title page, item "[22] Filed: Dec. 16, 1993" should read --[22] Filed: Nov. 16, 1993--.

IN THE ABSTRACT: Line 2, "cyclo-carbonate" should read ---cyclocarbonate--.

Col. 3, line 12, "$Al_2O$" should read --$Al_2O_3$--.

Col. 6, line 44, "Azeolite" should read --A-zeolite--; and line 61, "Chromatography" should read --chromatography--.

Col. 8, line 6, after "and" being a new paragraph; and line 39, "1-5" should read --1.5--.

UNITED STATES PATENT AND TRADEMARK OFFICE
CERTIFICATE OF CORRECTION

PATENT NO. : 5,436,362
DATED : July 25, 1995
INVENTOR(S) : Kondoh, et al

It is certified that error appears in the above-indentified patent and that said Letters Patent is hereby corrected as shown below:

Col. 10, line 67, after "the" insert --zeolite--.

Signed and Sealed this

Sixteenth Day of April, 1996

BRUCE LEHMAN

Attest:

Attesting Officer

Commissioner of Patents and Trademarks